United States Patent [19]

Lecomte et al.

[11] Patent Number: 5,510,107
[45] Date of Patent: Apr. 23, 1996

[54] PROCESS FOR THE MANUFACTURE OF A SOLID COSMETIC COMPOSITION USING PLASTER OF PARIS AND COSMETIC COMPOSITION THEREBY OBTAINED

[75] Inventors: Sophie Lecomte; Gwenola Le Gars, both of Paris, France

[73] Assignee: L'Oreal, Paris, France

[21] Appl. No.: 240,612

[22] Filed: May 11, 1994

[30] Foreign Application Priority Data

May 13, 1993 [FR] France .................. 93 05774

[51] Int. Cl.⁶ .................................................. A61K 7/48
[52] U.S. Cl. ....................... 424/401; 424/63; 424/64; 514/844
[58] Field of Search ................. 424/401, 63, 64; 514/844

[56] References Cited

U.S. PATENT DOCUMENTS

| | | | |
|---|---|---|---|
| 4,128,630 | 12/1978 | Hayashi et al. | 424/69 |
| 4,724,138 | 2/1988 | Duffy et al. | 514/844 |
| 4,804,538 | 2/1989 | Chen | 424/401 |
| 5,049,376 | 9/1991 | Murphy et al. | 424/63 |
| 5,049,594 | 9/1991 | Jeffs | 523/205 |
| 5,283,062 | 2/1994 | Elliott et al. | 424/63 |

FOREIGN PATENT DOCUMENTS

| | | |
|---|---|---|
| 0095889 | 12/1983 | European Pat. Off. . |
| 7203270 | 4/1973 | South Africa . |
| 8600798 | 2/1986 | WIPO . |

*Primary Examiner*—Thurman K. Page
*Assistant Examiner*—Sharon L. Howard
*Attorney, Agent, or Firm*—Cushman Darby & Cushman

[57] ABSTRACT

Process for the manufacture of a solid cosmetic composition using plaster of Paris, in which:

a pulverulent mixture (P) consisting of:

1) calcium sulphate hemihydrate ($CaSO_4.\frac{1}{2} H_2O$) in powder form, 2) a hydrophobic fraction (OF) comprising at least one fatty substance and/or at least one pulverulent substance treated by coating or chemical grafting so as to give it hydrophobic properties, 3) a hydrophilic fraction (IF) in powder form, is prepared, the weight proportion IF/OF being between 0.08 and 7.5;

an aqueous phase (AP) in liquid form is prepared;

the pulverulent mixture (P) and the aqueous phase (AP) are headed in a weight proportion P/AP of between 0.2 and 2, so as to obtain a pourable mixture;

the pourable mixture is run into a mould;

it is left to harden by hydration of the calcium sulphate hemihydrate to calcium sulphate dihydrate ($CaSO_4.2H_2O$), and the product is removed from the mould.

27 Claims, No Drawings

PROCESS FOR THE MANUFACTURE OF A SOLID COSMETIC COMPOSITION USING PLASTER OF PARIS AND COSMETIC COMPOSITION THEREBY OBTAINED

The present invention relates to a process for the manufacture of a solid cosmetic composition using plaster of Paris, and to a cosmetic composition obtained by this process.

It is known to manufacture cosmetic compositions in solid form using plaster of Paris. These cosmetic compositions can be, in particular, eye shadows, blushers and face or body powders; they can be in the form of sticks, pencils or cakes. The use of plaster of Paris for the manufacture of these solid compositions is, for example, described in EP-A 0,036,698. According to the known processes, a phase containing plaster of Paris is mixed with an aqueous phase to obtain a paste which is shaped by moulding, the hydration reaction of the plaster of Paris (calcium sulphate hemihydrate) to calcium sulphate dihydrate causing solidification of the composition. The use of plaster of Paris as a solidifying agent is advantageous, since it enables the compaction operation, which is normally needed for obtaining a composition in solid form from pulverulent products, to be replaced by a moulding operation, the implementation of which is simpler and cheaper and enables a greater variety of forms to be obtained.

However, the use of plaster of Paris for obtaining a solid cosmetic composition causes a problem: it is difficult to incorporate hydrophobic starting materials that are difficult to wet, whose presence is, however, essential for the cosmetic quality of the finished products, in such a composition. In effect, for example, it is necessary to introduce fatty substances, or compounds having the properties of fatty substances such as powders coated with a fatty substance, in order to make the cosmetic composition pleasant to apply and provide it with adhesion to the skin; it is often desirable as well to introduce hydrophobic powders such as talc so that the composition glides smoothly over the skin. In the presence of these hydrophobic compounds, proper wetting of the powder does not take place, thereby giving rise to some degree of heterogeneity of the solidified composition. After drying, the product contains particles or agglomerates which are troublesome on application, or else the product contains voids caused by inclusions of air on mixing the composition with water, which can make the moulded product brittle and impair its appearance.

To avoid this drawback, it has been proposed in WO86/00,798 to introduce the fatty substances in the form of an emulsion in water. This process hence necessitates an additional step of emulsification of the fatty substances. Furthermore, the amount of surfactants needed becomes very high as soon as hydrophobic pulverulent fillers are used, since surfactants have to be introduced both to emulsify the fatty substances and to wet the hydrophobic powders. In addition, the solid product obtained is not satisfactory, since it is soft and brittle. It has also been proposed to disperse the fatty substances in a solvent (see EP-A-0,095,889): however, the presence of a solvent interferes with the setting of the plaster of Paris, furthermore, the problem of wetting on mixing with the aqueous phase is not solved.

According to the present invention, it has been found that, by mixing an almost pulverulent mixture containing plaster of Paris, hydrophobic compounds and a sufficient proportion of hydrophilic pulverulent compounds with an aqueous phase, wetting of the pulverulent mixture is satisfactory without it being necessary to add large amounts of surfactant; and, in addition, that the solid composition obtained displays neither voids nor agglomerates. Furthermore, this process has the advantage of making it possible to incorporate, in a high proportion in the compositions, "diffusing" fillers such as silica and silicone beads, or expanded microspheres made of thermoplastic material having a density of 15 to 200 kg/m$^3$, for instance those made of acrylonitrile/vinylidene chloride/methyl methacrylate terpolymer marketed by the company "CASCO-NOBEL" under the name "EXPANCEL 551 DE".

To determine whether, according to the invention, a pulverulent subs range is "hydrophobic" or "hydrophilic", the test defined below is performed. A test tube 20 mm in diameter is filled with 20 ml of water. 2 grams of powder are poured into the tube without shaking and the behavior of the powder is observed over not more than 5 minutes. If the powder remains entirely at the surface, it is considered to be "hydrophobic". Otherwise it is considered to be "hydrophilic".

According to the invention, it is possible either to mix all of the different compounds constituting the pulverulent mixture, or to perform a premixing of the different hydrophobic compounds and a premixing of the different hydrophilic compounds. Irrespective of the mode of preparation used, the set of hydrophobic compounds will be designated hereinafter in the description by the term "hydrophobic fraction", and the set of hydrophilic compounds by the term "hydrophilic fraction".

The subject of the present invention is hence a process for the manufacture of a solid cosmetic composition using plaster of Paris, characterized in that:

a pulverulent mixture (P) consisting of:
  1) calcium sulphate hemihydrate ($CaSO_4.\frac{1}{2} H_2O$) in powder form,
  2) a hydrophobic fraction (OF) comprising at least one fatty substance and/or at least one pulverulent substance treated by coating or chemical grafting so as to give it hydrophobic properties,
  3) a hydrophilic fraction (IF) in powder form, is prepared, the weight proportion IF/OF being between 0.08 and 7.5, and preferably between 0.40 and 3.25;

an aqueous phase (AP) in liquid form is prepared;

the pulverulent mixture (P) and the aqueous phase (AP) are headed in a weight proportion P/AP of between 0.2 and 2, and preferably between 0.5 and 1.5, so as to obtain a pourable mixture;

the pourable mixture is run into a mould;

it is left to harden by hydration of the calcium sulphate hemihydrate to Calcium sulphate dihydrate ($CaSO_4.2H_2O$), and the product is removed from the mould.

The calcium sulphate hemihydrate used according to the invention can be in its $\alpha$ form and/or in its $\beta$ form. It may be mixed with at least one setting time-modifying agent such as retarders, for instance, sodium citrate, and accelerators, for instance gypsum and sodium sulphates. The amount of calcium sulphate hemihydrate represents, appropriately, 15 to 35% by weight, and preferably 20 to 30% by weight, of the pulverulent mixture (P).

The hydrophobic fraction (OF) necessarily contains at least one fatty substance and/or at least one powder treated by coating or chemical grafting so as to give it the cosmetic properties of a fatty substance.

The fatty substances which are usable are all those generally used in cosmetic compositions. Among these fatty substances, there may be mentioned oils of mineral origin such as liquid paraffins oils of animal origin such as lanolin; oils of vegetable origin such as jojoba oils; esters of a carboxylic acid and a $C_{10}$–$C_{22}$ fatty alcohol or with a lower alcohol, such as triisocetyl citrate, isopropyl myristate, tridecyl neopentanoate; fatty alcohols such as oleyl alcohol, isostearyl alcohol, octyldodecanol; silicone oils, gums or waxes such as alkyl dimethicones; and fluorinated oils and their derivatives, in particular silicone derivatives.

According to the invention, the fatty substances can contain at least one additive and/or at least one cosmetic active agent which is fat-soluble. Among these additives or active agents, there may be mentioned polymers such as hexadecene/vinylpyrrolidone copolymer, sunscreen agents, perfumes, preservatives, antioxidants and vitamins which are fat-soluble.

The powders treated by coating or chemical grafting so as to give them the cosmetic properties of fatty substances are products which are pulverulent in nature, either hydrophobic or hydrophilic, which have been treated with hydrophobic products, among which there may be mentioned, for example, silicones, lipoamino acids, metallic soaps, fluorinated derivatives, mineral oils, lecithin, isopropyl triisostearoyltitanate, polyethylene and collagen and its derivatives.

The hydrophobic fraction (OF) can optionally contain powders which are hydrophobic by nature, that is to say without it being necessary to treat them, such as:

talc, which is a hydrated magnesium silicate, powders of hydrophobic polymers, such as nylon the polyamide powder, for example that marketed under the name "ORGASOL 2002 ED NAT COS" by the company "ATOCHEM", polyethylene powder, for example that marketed under the name "COATHYLENE HA 1681" by the company "PLAST LABOR"; expanded microspheres made of thermoplastic material, for example that marketed under the name "EXPANCEL 551 DE" by the company "CASCO-NOBEL", polyfluorinated powders, in particular of polytetrafluoroethylene, for example that marketed under the name "MP 1400" by the company "DU PONT DE NEMOURS", silicone powders, for example that marketed Under the name "TOSPEARL" by the company "TOSHIBA", acrylic copolymer powders such as that marketed under the name "POLYTRAP Q5 6603" by the company "DOW CHEMICAL", or alternatively polystyrene powders such as that marketed under the name "POLYSPHERE 3 000 SP" by the company "PRESPERSE", lipoamino acids, for example lauroyllysine, boron nitride, and metallic soaps of $C_8$–$C_{22}$, and more especially $C_{12}$–$C_{18}$, carboxylic acids, for example zinc and magnesium stearates, zinc laurate or magnesium myristate.

In the hydrophobic fraction (OF), the fatty substance(s) and/or the treated pulverulent substance(s) represent (s) at least 1% by weight. The hydrophobic fraction (OF) represents 10 to 60% by weight, and preferably 20 to 45% by weight, of the pulverulent mixture (P).

The hydrophilic fraction (IF) advantageously contains at least one untreated hydrophilic uncolored filler and/or at least one hydzophilic treated uncolored filler and/or at least one pigment.

Among hydrophilic uncolored fillers, there may be mentioned:

micas, which are aluminum potassium silicates of miscellaneous compositions, of natural origin, such as muscovite, phlogopite, lepidolite, biotite and sericite, or of synthetic origin, bismuth oxychloride, silicas, which can be in the form of plates or spheres, such as the silica marketed under the name "SILICA BEADS SB 700" by the company "MIYOSHI", powders of hydrophilic polymers, which are of synthetic origin, for instance polyacrylates, for example that marketed under the name "MICROPEARL M 100" by the company "MATSUMOTO", acrylic polyamides such as that marketed by the company "ORIS" and polyurethanes such as that marketed under the name "PLASTIC POWDER D 800" by the company "TOSHIKI" or which are of natural origin, for instance cellulose or starch derivatives, for example porous cellulose microspheres, kaolin, which is a hydrated aluminum silicate, hydroxyapatite, zinc or titanium oxides, for their covering power in particular, it being possible for these products to be used in the nanopigment state for their screening effect, calcium carbonate, and magnesium carbonate and magnesium bicarbonate, which facilitate the binding of perfumes.

The hydrophilic treated fillers are pulverulent substances treated by coating or chemical grafting to render their surface hydrophilic, using substances such as chitosan, titanium dioxide, silica or hydrophilic polymers, in particular poly(sulphonic ester)s or poly(quaternary ammonium) compounds.

The pigments can be any hydrophilic colored pigment which is usable in cosmetics. These pigments can be inorganic or organic pigments or nacreous pigments, coated or otherwise. Among inorganic pigments, there may be mentioned, as an example:

black, yellow, red and brown iron oxides, coded in the Color Index under references CI 77499, CI 77492 and CI 77491;

manganese violet (CI 77742);

ultramarine blue (CI 77007);

ultramarine violet (CI 77007);

chromium oxide (CI 77288);

hydrated chromium oxide (CI 77289); and ferric blue (CI 77510).

Among organic pigments, special mention may be made of the pigments:

D & C red no. 3 (CI 45430:1)

D & C red no. 6 (CI 15850:2)

D a C red no. 7 (CI 15850:1)

D & C red no. 9 (CI 15585:1)

D & C red no. 13 (CI 15630:3)

D & C red no. 19 (CI 45170)

D & C red no. 21 (CI 45380:2)

D & C red no. 27 (CI 45410:1)

D & C red no. 30 (CI 73360)

D & C red no. 36 (CI 12085)

carbon black (CI 77266) and lakes based on carmine (CI 75470).

The nacreous pigments may be chosen, in particular, from white nacreous pigments such as titanium oxide- or bismuth oxychloride-coated mica. It is also possible to use colored nacreous pigments such as titanium mica colored with iron oxides, titanium mica colored with ferric blue or with chromium oxide, or titanium mica colored with an organic pigment of the type mentioned above, as well as nacreous pigments based on bismuth oxychloride.

The hydrophilic fraction (IF) generally represents from 5 to 75% by weight of the pulverulent mixture (P), and preferably from 25 to 60% by weight.

The pulverulent mixture (P) can optionally contain at least one surfactant, which may assist in the wetting and dipersion of the pulverulent mixture. The surfactant can be nonionic, for instance oxyethylenated sorbitan esters, cationic, for instance quaternary ammonium salts, or amphoteric, for instance betane derivatives. The amount of surfactant introduced does not exceed 5% by weight of the pulverulent mixture (P).

The aqueous phase (AP) necessarily contains a sufficient amount of water to hydrate the plaster of Paris to calcium sulphate dihydrate. It optionally contains at least one water-soluble or -dispersible additive. These additives can be:

- water-soluble cosmetic active agents such as glycerol, polyethylene glycol and sunscreen agents, or water-soluble adjuvants such as preservatives and antioxidants;
- water-soluble or water-dispersible polymers such as poly(quaternary ammonium) compounds, polyacrylates, vinylpyrrolidone derivatives, chitosan or polyholosides, it being possible for these polymers to be introduced in the form of a latex;
- water-soluble or water-dispersible waxes such as polyether silicone or a dispersible polyethylene;
- water-soluble or -dispersible surfactants which can be nonionic, cationic or amphoteric, for example dimethicone copolyols and ethers of oxyethylenated fatty alcohols.

The subject of the present invention is also the solid cosmetic composition containing plaster of Paris obtained by the process described above.

This composition contains from 15 to 354 by weight of calcium sulphate dihydrate ($CaSO_4 \cdot 2H_2O$), and preferably from 20 to 30% by weight; 10 to 60% by weight, and preferably 20 to 45% by weight, of hydrophobic fraction (OF) as described above; 5 to 754 by weight, and preferably 20 to 654 by weight, of hydrophilic fraction (IF) as described above, the fatty substance(s) and/or the pulverulent- substance(s) treated by coating or chemical grafting so as to become hydrophobic representing at least 0.14 by weight of the composition.

This composition optionally contains at most 10% by weight of surfactant and/or at most 10% by weight of cosmetic additives previously dispersed or solubilized in water, and/or at most 10% by weight of setting time-modifying agent.

The examples given below, as a guide and without implied limitation, will enable a better understanding of the invention to be gained.

EXAMPLE 1: Blusher

A pulverulent mixture (P) having the following formulation (in grams) is prepared:

| | | | |
|---|---|---|---|
| 1) | Plaster of Paris ($CaSO_4 \cdot \frac{1}{2}H_2O$) | | 25 |
| 2) | Hydrophobic fraction (OF) of which: | | 40 |
| | talc | | 25 |
| | lauroyllysine-coated talc marketed under the name "EP 90025 TALC TREATED" by the company "MEARL" | | 10 |
| | expanded microspheres marketed under the name "EXPANCEL 551 DE" by the company "CASCO-NOBEL" | | 5 |
| 3) | Hydrophilic fraction (IF) of which: | | 35 |
| | mica | | 24 |
| | calcium carbonate | | 5 |
| | titanium dioxide | | 2 |
| | red iron oxide | | 3.5 |
| | black iron oxide | | 0.5 |

The weight ratio IF/OF is 0.87.

Simultaneously, an aqueous phase (AP) having the following formulation (in grams) is prepared:

| | |
|---|---|
| water | 165 |
| surfactant marketed under the name "GLUCQUAT 100" by the company "AMERCHOL" | 4.5 |
| preservative | 0.1 |

The pulverulent mixture (P) and the aqueous phase (AP) are mixed in a mixer with slow stirring for 5 min; a fluid paste is obtained, which is poured into a mould. After 12 hours, the stick obtained is removed from the mould and allowed to dry. A blusher having the following composition (in % by weight) is obtained:

| | |
|---|---|
| calcium sulphate dihydrate | 23.9 |
| talc | 23.9 |
| lauroyllysine-coated talc marketed under the name "EP 90025 TALC TREATED" by the company "MEARL" | 9.6 |
| expanded microspheres marketed under the name "EXPANCEL 551 DE" by the company "CASCO-NOBEL" | 4.8 |
| mica | 22.9 |
| calcium carbonate | 4.8 |
| titanium dioxide | 1.9 |
| red iron oxide | 3.5 |
| black iron oxide | 0.5 |
| surfactant marketed under the name "GLUCQUAT 100" by the company "AMERCHOL" | 4.3 |
| preservative | 0.1 |

The blusher obtained contains neither aggregates nor voids; it is hard but friable and can be applied easily,

EXAMPLE 2: Face powder

A paste having the formulation given below in grams is prepared as in Example 1, which paste, after moulding and drying, gives a dry finished product having the composition shown below (in % by weight):

| CONSTITUENTS | Paste (in grams) | Dry finished product (in % by weight) |
|---|---|---|
| Pulverulent mixture (P) | | |
| 1) Plaster of Paris ($CaSO_4 \cdot \frac{1}{2} H_2O$) | 30 | 28.65* |

-continued

| CONSTITUENTS | Paste (in grams) | Dry finished product (in % by weight) |
|---|---|---|
| 2) Hydrophobic fraction (OF) | | |
| talc | 39.5 | 37.7 |
| mica coated with silicone by the SI treatment, marketed by the company "MIYOSHI" | 10 | 9.6 |
| nylon powder marketed under the name "ORGASOL 2002 ED NAT COS" by the company "ATOCHEM" | 10 | 9.6 |
| 3) Hydrophilic fraction (IF) | | |
| bismuth oxychloride | 5 | 4.8 |
| kaolin | 5 | 4.8 |
| mixture of iron oxides | 0.5 | 0.45 |
| Aqueous phase (AP) | | |
| water | 125 | — |
| surfactant marketed under the name "BRIJ 99" by the company "ICI" | 4.5 | 4.3 |
| gum arabic | 0.1 | 0.1 |

*in the form of ($CaSO_4 \cdot 2H_2O$)

After moulding and drying, the product obtained takes the form of a convex cake, which can be used with a powder puffs it contains neither agglomerates nor voids. The paste can also be moulded in the form of a pencil which can be used for concealing shadows under the eyes.

EXAMPLE 3: Face powder

A paste having the formulation given below in grams is prepared as in Example 1, which paste, after moulding and drying, gives a dry finished product having the composition shown below (in % by weight):

| CONSTITUENTS | Paste (in grams) | Dry finished product (in % by weight) |
|---|---|---|
| Pulverulent mixture (P) | | |
| 1) Plaster of Paris ($CaSO_4 \cdot \frac{1}{2} H_2O$) with accelerator (gypsum) | 28 | 26.8* |
| 2) Hydrophobic fraction (OF) | | |
| talc | 21.6 | 20.6 |
| boron nitride | 5 | 4.8 |
| surfactant marketed under the name "TWEEN 20" by the company "ICI" | 1 | 1 |
| perfume | 0.2 | 0.2 |
| polydimethylsiloxane marketed under the name "ABIL 10" by the company "GOLDSCHMIDT" | 5 | 4.8 |
| 3) Hydrophilic fraction (IF) | | |
| mica | 22 | 21 |
| polymethylmethacrylate powder marketed under the name "MICROPEARL M 305" by the company "MATSUMOTO" | 17 | 16.3 |
| mixture of iron oxides | 0.2 | 0.2 |
| Aqueous phase (AP) | | |
| water | 125 | — |
| polyethylene glycol containing 8 ethylene oxide units | 4.5 | 4.3 |

*in the form of ($CaSO_3 \cdot 2H_2O$)

The powder obtained takes the form of a rectangular cake, which can be used with a powder puff or a brush and displays neither agglomerates nor voids.

EXAMPLE 4: Eyeshadow

A paste having the formulation given below in grams is prepared as in Example 1, which paste, after moulding and drying, gives a dry finished product having the composition shown below (in % by weight):

| CONSTITUENTS | Paste (in grams) | Dry finished product (in % by weight) |
|---|---|---|
| Pulverulent mixture (P) | | |
| 1) Plaster of Paris ($CaSO_4 \cdot \frac{1}{2} H_2O$) | 20 | 19.9* |
| 2) Hydrophobic fraction (OF) | | |
| talc | 23 | 22.9 |
| liquid paraffin | 0.9 | 0.9 |
| hexadecene/vinylpyrrolidone copolymer marketed under the name "GANEX V216" by the company "ISP" | 0.1 | 0.1 |
| 3) Hydrophilic fraction (IF) | | |
| silica microbeads marketed under the name "SILICA BEADS SB 150" by the company "MIYOSHI" | 20 | 19.9 |
| bismuth oxychloride | 10 | 9.9 |
| titanium mica | 20 | 19.9 |
| ferric blue | 6 | 5.9 |
| Aqueous phase (AP) | | |
| water | 124 | — |
| preservatives | 0.2 | 0.2 |
| polyvinylpyrrolidone | 0.4 | 0.4 |

*in the form of ($CaSO_4 \cdot 2H_2O$)

block, which can be used with the finger or with an applicator and which displays neither agglomerates nor voids.

We claim:

1. A process for the manufacture of a solid cosmetic composition containing plaster of Paris, said process comprising
   (a) preparing a pulverulent mixture of
      (i) calcium sulphate hemihydrate in powder form,
      (ii) a hydrophobic fraction comprising at least one fatty substance or at least one pulverulent substance treated by coating or chemical grafting so as to impart thereto hydrophobic properties, or a mixture thereof, and
      (iii) a hydrophilic fraction, the weight proportion (iii)/(ii) being between 0.08 and 7.5,
   (b) preparing an aqueous phase in liquid form;
   (c) kneading said pulverulent mixture and said aqueous phase in a weight proportion of said pulverulent mixture/aqueous phase between 0.2 and 2 so as to obtain a pourable mixture;
   (d) introducing said pourable mixture into a mold;
   (e) hardening said mixture in said mold by hydration of said calcium sulphate hemihydrate to calcium sulphate dihydrate; and
   (f) removing the product resulting from step (e) from said mold.

2. The process of claim 1 wherein said pulverulent mixture and said aqueous phase are kneaded in step (c) in a weight proportion between 0.5 and 1.5.

3. The process of claim 1 wherein the amount of water supplied in said aqueous phase is at least sufficient to hydrate all said calcium sulphate hemihydrate of said pulverulent mixture to calcium sulphate dihydrate.

4. The process of claim 1 wherein the weight proportion of said hydrophilic fraction relative to said hydrophobic fraction ranges between 0.40 and 3.25.

5. The process of claim 1 wherein said calcium sulphate hemihydrate is mixed with at least one setting time-modifying agent.

6. The process of claim 1 wherein said calcium sulphate hemihydrate represents from 15 to 35 weight percent of said pulverulent mixture.

7. The process of claim 1 wherein said fatty substance is selected from the group consisting of a mineral oil, an animal oil, a vegetable oil, an ester of a carboxylic acid with a $C_{10}$–$C_{22}$ fatty alcohol, an ester of a carboxylic acid with a lower alcohol, a fatty alcohol, a silicone oil, a silicone gum, a silicone wax and a fluorinated oil.

8. The process of claim 7 wherein said fatty substance contains at least one additive or at least one active agent or a mixture thereof, which is fat-soluble.

9. The process of claim 1 wherein said pulverulent substance treated by coating or chemical grafting is selected from the group consisting of a powder treated with a silicone, a powder treated with a lipoamino acid., a powder treated with a metallic soap, a powder treated with a fluorinated derivative, a powder treated with a mineral oil, a powder treated with lecithin, a powder treated with isopropyl triisostearoyltitanate, a powder treated with polyethylene and a powder treated with collagen.

10. The process of claim 1 wherein said hydrophobic fraction of said pulverulent mixture contains at least one hydrophobic pulverulent substance not treated by coating or grafting and being selected from the group consisting of talc, a powder of a hydrophobic polymer, a lipoamino acid, boron nitride and a metallic soap of a $C_8$–$C_{22}$ carboxylic acid.

11. The process of claim 10 wherein said powder of a hydrophobic polymer is selected from the group consisting of a polyamide powder, a polyethylene powder, an expanded microsphere of a thermoplastic material, a polyfluorinated powder, a silicone powder, an acrylic copolymer powder and a polystyrene powder.

12. The process of claim 10 wherein said powder of a hydrophobic polymer is a powder of an acrylonitrile/vinylidene chloride/methyl methacrylate copolymer.

13. The process of claim 1 wherein said fatty substance or said pulverulent substance treated by coating or chemical grafting, or said mixture thereof represents at least 1 weight percent of said hydrophobic fraction.

14. The process of claim 1 wherein said hydrophobic fraction represents from 10 to 60 weight percent of said pulverulent mixture.

15. The process of claim 1 wherein said hydrophilic fraction comprises a member selected from the group consisting of an untreated hydrophilic uncolored filler, a hydrophilic treated uncolored filler, a non-coated pigment and a coated pigment.

16. The process of claim 15 wherein said untreated hydrophilic uncolored filler is selected from the group consisting of a mica, bismuth oxychloride, a silica, a powder of a hydrophilic polymer, kaolin, hydroxyapatite, zinc oxide, titanium oxide, calcium carbonate, magnesium carbonate and magnesium bicarbonate.

17. The process of claim 15 wherein said hydrophilic treated uncolored filler is selected from the group consisting of chitosan, titanium dioxide, silica and a hydrophilic polymer.

18. The process of claim 15 wherein said pigment is selected from the group consisting of an inorganic pigment, an organic pigment and a nacreous pigment.

19. The process of claim 1 wherein said hydrophilic fraction represents from 5 to 75 weight percent of said pulverulent mixture.

20. The process of claim 1 wherein said hydrophilic fraction represents from 25 to 60 weight percent of said pulverulent mixture.

21. The process of claim 1 wherein said pulverulent mixture also contains at least one surfactant selected from the group consisting of a nonionic surfactant, a cationic surfactant, an amphoteric surfactant and mixtures thereof.

22. The process of claim 1 wherein said aqueous phase contains at least one additive, said additive being a water-soluble or water-dispersible additive.

23. The process of claim 22 wherein said additive is selected from the group consisting of a water-soluble cosmetic active agent, a polymer, a wax, a water-soluble surfactant and a water-dispersible surfactant.

24. A solid cosmetic composition obtained by the process of claim 1.

25. A solid cosmetic composition comprising 15 to 35 weight percent of calcium sulphate dihydrate; 10 to 60 weight percent of a hydrophobic fraction comprising at least one fatty substance or at least one pulverulent substance treated by coating or chemical grafting so as to impart thereto hydrophobic properties, or a mixture thereof; 5 to 75 weight percent of a hydrophilic fraction; said fatty substance or said pulverulent substance treated by coating or chemical grafting, or a mixture thereof, represents at least 0.1 percent by weight of said composition.

26. The composition of claim 25 wherein said calcium sulphate dihydrate is present in an amount ranging from 20 to 30 weight percent; said hydrophobic fraction is present in an amount ranging from 20 to 45 weight percent and said hydrophilic fraction is present in an amount ranging from 20 to 65 weight percent.

27. The composition of claim 25 which also contains (i) at most 10 weight percent of a surfactant or (ii) at most 10 weight percent of a cosmetic additive previously dispersed or solubilized in water, or (iii) at most 10 weight percent of a setting time-modifying agent, or (iv) mixtures thereof.

* * * * *